US00PP11094P

United States Patent [19]

Fear et al.

[11] Patent Number: Plant 11,094

[45] Date of Patent: Oct. 12, 1999

[54] RASPBERRY PLANT NAMED 'HOLYOKE'

[75] Inventors: Carlos D. Fear, Aptos, Calif.; Mella-Dee M. Mayberry, Geeorgetown, Del.

[73] Assignee: Sweetbriar Development, Inc., Watsonville, Calif.

[21] Appl. No.: 09/052,490

[22] Filed: Mar. 31, 1998

[30] Foreign Application Priority Data

Mar. 9, 1998 [EP] European Pat. Off. ..... 98/0346

[51] Int. Cl.[6] ..... A01H 5/00

[52] U.S. Cl. ..... Plt./204

[58] Field of Search ..... Plt./204

[56] References Cited

U.S. PATENT DOCUMENTS

P.P. 7,528 5/1991 Ackerman ..... Plt./204

*Primary Examiner*—Howard J. Locker
*Assistant Examiner*—Wendy A Baker
*Attorney, Agent, or Firm*—Pennie & Edmonds LLP

[57] ABSTRACT

The present invention relates to a new and distinct cultivar of red raspberry plant named 'Holyoke'. The new cultivar is distinguished from other red fruited raspberry cultivars by its large, glossy fruit of bright color, very attractive fruit and its high yielding capacity on both primocane and floricane crops. 'Holyoke' is distinguished from its pollen parent by having firmer, shinier fruit and being earlier in the primocane crop. The new cultivar is distinguished from its seed parent by having a lighter color and firmer fruit.

2 Drawing Sheets

BACKGROUND OF THE INVENTION

The new cultivar of raspberry plant was developed from the hybridization of the selection 'H374-2' (an unpatented variety) as the seed parent with the selection 'E4-4' (an unpatented variety) as the pollen parent. The parents were crossed in the Fall of 1991, whereafter fruit and seed were collected to produce seedlings for field planting in Watsonville, Calif. in 1991. The new cultivar was selected from these seedlings in June 1993 for its large, bright color, shiny and glossy, very attractive fruit and its high yielding capacity on both primocane and floricane crops. It has excellent fruit firmness and is early in the primocane crop. The new cultivar has been asexually propagated by in vitro shoot tip culture, root sucker division and root cuttings at the Cassin Ranch in Santa Cruz county, Calif. and has been shown to maintain the desired and distinguishing characteristics after propagation over several generations.

SUMMARY OF THE INVENTION

The present invention provides a new and distinct cultivar of red raspberry plant named 'Holyoke'. The 'Holyoke' red raspberry plant produces a primocane crop which begins in mid to late July and continues until early November. The floricane crop begins in mid to late May and continues until early July. Both the primocane and floricane yields are high relative to other comparable varieties. The fruit of 'Holyoke' is large, glossy and attractive and remains consistently so throughout its harvest period. The fruit does not darken in color after harvest.

BRIEF DESCRIPTION OF THE DRAWINGS

The accompanying photographs show typical specimens of the primocane fruit, leaves and shoot of the new cultivar, in color as nearly true as it is reasonably possible to make in color illustrations of these characteristics.

DETAILED BOTANICAL DESCRIPTION

Figure 1:
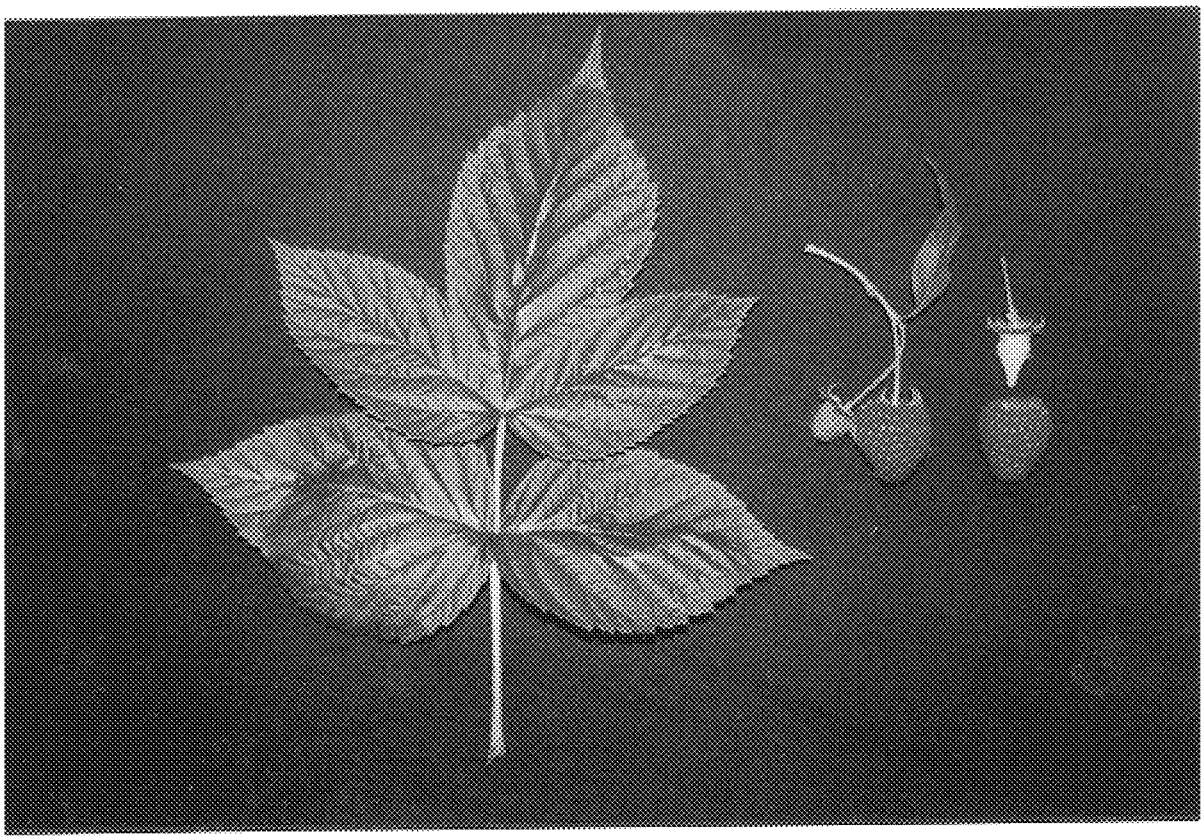
FIG. 1 is a photograph of a 'Holyoke' primocane mature leaf and fruit.
Figure 2:
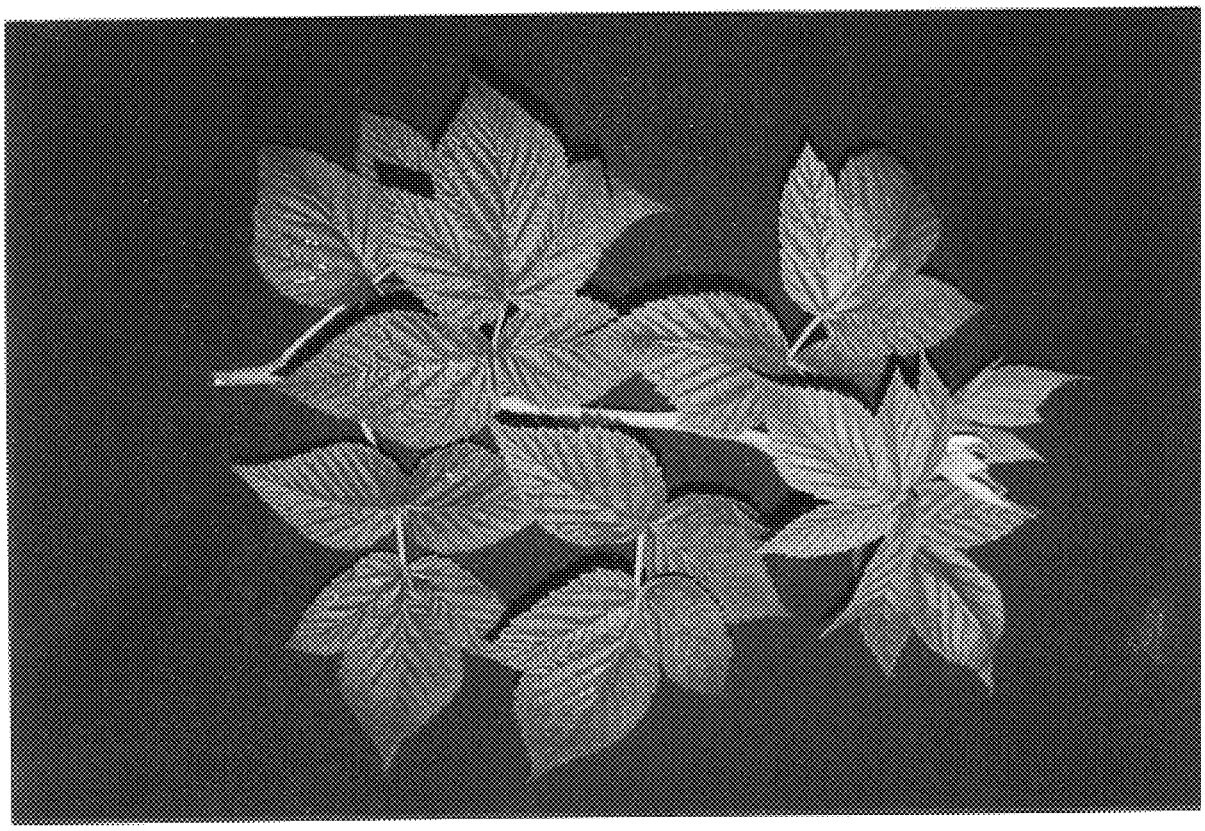
FIG. 2 is a photograph of a 'Holyoke' primocane shoot.

The following detailed description of the new raspberry cultivar, 'Holyoke', is based upon observations taken of plants and fruit grown in Watsonville, Calif. between 1994 and 1997, and is believed to apply to plants of the 'Holyoke' cultivar grown in similar conditions of soil and climate elsewhere.

Throughout this specification, color names beginning with a small letter signify that the name of the color, as used in common speech, is aptly descriptive. Color data beginning with a capital letter and followed by an alphanumeric code designating the color according to the R.H.S. Colour Chart published by The Royal Horticultural Society of London, England. Color designations, color descriptions, and other phenotypical descriptions may deviate from the stated values and descriptions depending upon variation in environmental, seasonal, climatic and cultural conditions.

Tables 1 and 2 provide information on the plant and fruit characteristics of the new cultivar 'Holyoke' compared with characteristics of the unpatented raspberry cultivars 'Heritage', 'Summit' and 'Amity'. The cultivars closest to the new cultivar 'Holyoke' are 'Heritage' and 'Amity' for their primocane cropping cycle, and 'Heritage' and 'Summit' for their floricane cropping cycle.

The new variety is particularly characterized and distinguished from other cultivars by its large, glossy and firm fruit.

The fruit color of 'Holyoke' is a bright, shiny, glossy red color of very attractive fruit with little color change after harvest.

The primocane yield of 'Holyoke' is high relative to the varieties 'Heritage' and 'Amity'. 'Holyoke' has a floricane yield similar to 'Amity' and 'Heritage'.

'Holyoke' is distinguishable from its pollen parent, selection 'E4-4', by having firmer, shinier fruit and being earlier in the primocane crop. The new cultivar is distinguished from its seed parent, selection 'H374.2', by having lighter color and firmer fruit.

ISOZYME ANALYSIS

In addition to the morphological description above, the new cultivar 'Holyoke' has been analyzed to obtain an indication of its genetic makeup to provide further means for identifying the new variety and distinguishing it from some other somewhat similar and/or related raspberry varieties. Specifically, leaf samples of 'Holyoke', and the unpatented varieties 'Summit' and 'Heritage' were analyzed by electrophoresis for isozyme patterns of the enzymes phosphoglucoisomerase (PGI), malate dehydrogenase (MDH) and phosphoglucomutase (PGM) according to the procedure described by J. C. Cousineau and D. J. Donnelly, "Use of isozyme analysis to characterize raspberry cultivars and detect cultivar mislabeling", *Hort Science* 27:1023–1025 (1992). Isozyme characterization of the cultivar 'Holyoke' is presented in Table 3, with the letters representing the banding patterns for each enzyme as designated in the above-identified article.

DISEASE AND STRESS RESISTANCE

The cultivar has moderate resistance to late leaf rust. Resistance is unknown to powdery mildew and root rots. Cold tolerance of the new cultivar has not been established. Post harvest fruit rot resistance is average in comparison over many selections and varieties.

TABLE 1

PLANT CHARACTERISTICS OF 'HOLYOKE'

| | Holyoke | Heritage | Summit | Amity |
|---|---|---|---|---|
| General | | | | |
| Plant size | medium | large | small-medium | medium |
| Growth habit | erect | erect | semi-erect | erect |
| Productivity | high | medium | high | low-medium |
| Self-fruitfulness | self-fruitful | self-fruitful | self-fruitful | self-fruitful |
| Primocane fruiting | | | | |
| percent of cane flowering as primocane | ~15–30 | ~5–20 | ~40–50 | ~20–35 |
| percent of total yield | ~60–70 | ~40–60 | ~50–70 | ~40–50 |
| Number of young shoots | medium | medium | few | many |
| Canes | | | | |
| Primocanes | | | | |
| number fruiting laterals/cane | 7–21 (mean 14) | 2–14 (mean 8) | 9–15 (mean 12) | 6–14 (mean 10) |
| number of canes/crown | 2–6 (mean 4) | 3–5 (mean 4) | 2–7 (mean 3) | 1–6 (mean 3) |
| young shoot pigmentation | weak intensity red | medium intensity red | medium intensity red | medium intensity red |
| length (cm) | 161–228 (mean 197) | 182–230 (mean 208) | 137–212 (mean 164) | 135–208 (mean 168) |

TABLE 1-continued

PLANT CHARACTERISTICS OF 'HOLYOKE'

| | Holyoke | Heritage | Summit | Amity |
|---|---|---|---|---|
| diameter (end of 1st year) | | | | |
| cane base (cm) | 1.1–1.6 (mean 1.3) | 0.9–1.4 (mean 1.2) | 0.8–1.3 (mean 1.1) | 0.8–1.5 (mean 1.1) |
| central ⅓ of cane (cm) | 0.9–1.2 (mean 1.1) | 0.8–1.1 (mean 1.0) | 0.7–1.0 (mean 0.8) | 0.6–1.0 (mean 0.8) |
| time of shoot emergence | early | very late | late | medium |
| prickles | | | | |
| pigmentation | green-brownish green | green-brownish-green | brownish purple-purple | purple |
| density on young shoots | medium | dense | sparse | sparse |
| attitude of tip | horizontal | downward | downward | horizontal |
| size | medium | medium | medium | small |
| texture | heavy | rigid | heavy | heavy |
| presence and distribution on petioles | regularly distributed | regularly distributed | regularly distributed | regularly distributed |
| pubescence on canes | medium | absent or very weak | medium | medium |
| internodal distance (cm) | | | | |
| (at central ⅓ of cane) | 4.0–7.7 (mean 5.3) | 3.0–6.0 (mean 4.7) | 3.2–7.5 (mean 4.8) | 3.0–6.5 (mean 5.0) |
| lenticels | not visible | not visible | not visible | not visible |
| Floricanes | | | | |
| number nodes/lateral branch | 9–16 | 10–14 | 10–15 | 12–19 |
| number of flowers/node | 1–2 | 1–4 | 2–6 | 1–2 |
| Leaves | | | | |
| Arrangement | compound | compound | compound | compound |
| Relief between veins | strong | very weak | medium | medium |
| Cross section | variable, convex-concave | concave | flat | concave-flat |
| Leaflet number | usually 3 | 3–5 | usually 5 | usually 3 |
| Terminal leaflet | | | | |
| length (cm) | 13.6 | 14.6 | 12.4 | 13.7 |
| width (cm) | 12.2 | 7.8 | 7.2 | 12.1 |
| shape | lobed | ovate | ovate | lobed |
| tip | acuminate | acuminate | acuminate | acuminate |
| base | cordate | acute | rounded | cordate |
| margin | doubly serrate | doubly serrate | doubly serrate | doubly serrate |
| Lateral leaflets (basal pair) | | | | |
| overlap | touching | free | overlapping | overlapping |

TABLE 1-continued

PLANT CHARACTERISTICS OF 'HOLYOKE'

| | Holyoke | Heritage | Summit | Amity |
|---|---|---|---|---|
| orientation | opposite | opposite | opposite | opposite |
| shape | ovate | oblique | ovate-lobed | ovate-lobed |
| tip | acuminate | acuminate | acuminate | acuminate |
| base | oblique-rounded | oblique | oblique-rounded | oblique |
| margin | doubly serrate | doubly serrate | doubly serrate | doubly serrate |
| length (cm) | 10.8 | 14.7 | 11.6 | 11.7 |
| width (cm) | 8.1 | 8.6 | 7.7 | 8.2 |
| Rachis length between terminal leaflet and adjacent lateral leaflets (cm) | 3.0–4.1 (mean 3.4) | 0.8–2.2 (mean 1.5) | 0.5–1.8 (mean 1.2) | 2.4–3.9 (mean 3.0) |
| Glossiness | glossy | medium | medium | dull |
| Color | | | | |
| face | medium 137A | medium 137A, 139A | medium 137A | medium 147A |
| underside | 138B | 148C, 191B | 191B | 191A |
| Petiole | | | | |
| length (cm) | 5.0–7.8 (mean 6.7) | 6.6–8.5 (mean 7.6) | 5.8–8.9 (mean 7.4) | 4.0–8.2 (mean 6.0) |
| pigmentation of upper surface | unpigmented | lightly | lightly | lightly |
| pigmentation of underside | unpigmented | unpigmented | lightly | unpigmented |
| Petiolule length | very short | very short | short | very short |
| Stipule orientation | erect | erect | erect-clasping | erect-clasping |
| Flowers | | | | |
| Flower color | white | white | white | white |
| Flowering period | | | | |
| primocane | mid June-early October | mid June-early October | early June-mid September | early June-early October |
| floricane | early April-early June | early April-early June | early April-early June | early to mid March-early June |
| Flower size | medium | small | medium | large |
| Petal | | | | |
| length (cm) | 0.8–1.0 | 0.7–0.8 | 0.7–0.9 | 0.7–1.0 |
| width (cm) | 0.3–0.4 | 0.3 | 0.3–0.4 | 0.3–0.5 |
| Pedicel | | | | |
| coloration | absent or very weak intensity red | present, strong intensity, red | present, strong intensity, red | present, strong intensity, red |
| length | medium | medium | medium | long |
| Productivity | | | | |
| Primocane | ~9.2 t/acre | ~5.1 t/acre | ~7.3 t/acre | ~6.4 t/acre |

TABLE 1-continued

PLANT CHARACTERISTICS OF 'HOLYOKE'

| | Holyoke | Heritage | Summit | Amity |
|---|---|---|---|---|
| Floricane | ~4.1 t/acre | ~4.1 t/acre | ~2.9 t/acre | ~5.1 t/acre |

TABLE 2

FRUIT CHARACTERISTICS OF 'HOLYOKE'

| | Holyoke | Heritage | Summit | Amity |
|---|---|---|---|---|
| Fruit | | | | |
| Harvest season | | | | |
| primocane | mid to late July-early November | late July-mid November | mid July-late October | mid July-mid November |
| floricane | mid to late May-early July | mid May-mid July | mid May-mid July | late April -mid July |
| Color | Light-Medium Red | Medium Red | Medium Red | Medium Red |
| immature | 44C | 53A | 46A | 46A |
| maturing | 45A | 45A, 46D | 45A | 47A |
| mature | 46A | 44C | 42B | 42B |
| Glossiness | strong | medium | medium | medium |
| Dimensions | | | | |
| weight (g/fruit) | | | | |
| primocane | 4.0–5.1 (mean 4.4) | 2.7–2.9 (mean 2.8) | 2.5–3.3 (mean 2.8) | 2.7–3.7 (mean 3.2) |
| floricane | 3.2–4.2 (mean 3.8) | 2.3–2.7 (mean 2.6) | 2.5–2.8 (mean 2.6) | 3.0–3.4 (mean 3.2) |
| length (primocane) (mm) | 22.2–28.6 (mean 25.3) | — | 17.5–25.4 (mean 20.2) | 17.5–22.2 (mean 20.1) |
| width (primocane) (mm) | 19.8–27.0 (mean 23.9) | — | 18.3–23.0 (mean 20.4) | 15.9–23.0 (mean 20.2) |
| Soluble solids (%) | 8.2 | — | 9.4 | 9.7 |
| Titratable acidity | | | | |
| (% as citric acid) | 9.0 | — | 14.5 | 11.2 |
| Seeds | | | | |
| weight (mg) | 1.9 | — | 1.8 | 1.5 |
| Number druplets/fruit | 94–131 (mean 111) | 45–102 (mean 72) | 73–119 (mean 98) | 62–108 (mean 88) |

TABLE 3

ISOZYME BANDING PATTERNS OF 'HOLYOKE' COMPARED WITH 'HERITAGE' AND 'SUMMIT'

| | Isozyme and Pattern | | |
|---|---|---|---|
| Cultivar | PGI | MDH | PGM |
| Holyoke | D | K | C |
| Heritage | A | D | C |
| Summit | A | C | A |

We claim:

1. A new and distinctive cultivar of raspberry plant, as illustrated and described herein.

* * * * *